United States Patent [19]

Alessi

[11] Patent Number: 5,060,647
[45] Date of Patent: Oct. 29, 1991

[54] ENDOTRACHAEL TUBE

[76] Inventor: David M. Alessi, 3278 Wilshire Blvd., Los Angeles, Calif. 90010

[21] Appl. No.: 315,136

[22] Filed: Feb. 23, 1989

[51] Int. Cl.⁵ ............................................ A61M 16/00
[52] U.S. Cl. ............................ 128/207.14; 128/207.15
[58] Field of Search ...................... 128/207.14, 207.15, 128/200.26, 343, 10

[56] References Cited

U.S. PATENT DOCUMENTS

| 478,582 | 7/1982 | Ermold . | |
|---|---|---|---|
| 1,266,856 | 5/1918 | Ramsay | 128/207.14 |
| 3,756,244 | 9/1973 | Kinnear et al. . | |
| 3,880,168 | 4/1975 | Berman | 128/207.15 |
| 4,050,466 | 9/1977 | Koerbacher . | |
| 4,056,104 | 11/1977 | Jaffe | 128/207.15 |
| 4,141,364 | 2/1979 | Schultze | 128/207.15 |
| 4,156,428 | 5/1979 | Henkin | 128/207.15 |
| 4,166,467 | 9/1979 | Abramson | 128/207.14 |
| 4,178,939 | 12/1979 | Stephens | 128/207.15 |
| 4,275,724 | 6/1981 | Behrstock | 128/207.14 |
| 4,341,210 | 7/1982 | Elan | 128/207.15 |
| 4,425,911 | 1/1984 | Luomanen et al. | 128/DIG. 26 |

OTHER PUBLICATIONS

C. E. Lindholm, Experience with a New Orotrachael Tube, 1973, pp. 389-390, Acta Otolaryng 75.
Marinelli, M. D. et al., Endotrachael Prosthesis for Positive Pressure Ventilation After Tracheal Injury, Nov. 1981, pp. 805-806, Crital Care Medicine, vol. 9, No. 11.
G. A. R. Morgan & D. J. Steward, A Pre-Formed Paediatric Orotrachael Tube Design Based on Anatomical Measurements, Jan. 1982, pp. 9-11, Canadian Anaesthethists' Society Journal, vol. 29, No. 1.
Edward A. Loeser, M. D. et al., The Influence of Endotrachael Tube Cuff Design and Cuff Lubrication on Postoperative Sore Throat, Apr. 1983, pp. 376-379, The America Soceity of Anesthesiologists, Inc., vol. 58, No. 4.

Primary Examiner—Aaron J. Lewis
Attorney, Agent, or Firm—Pretty, Schroeder, Brueggemann & Clark

[57] ABSTRACT

A flexible endotracheal tube is described having a proximal end for attachment to an adapter or to another tube. A distal end has an opening for extending past the vocal cords of a patient. An intermediate portion passes between the vocal cords wherein the intermediate portion comprises an outer shape in transverse cross section defined in part by two substantially straight sides converging to a tip. A mouth guard for the endotracheal tube is also described.

13 Claims, 2 Drawing Sheets

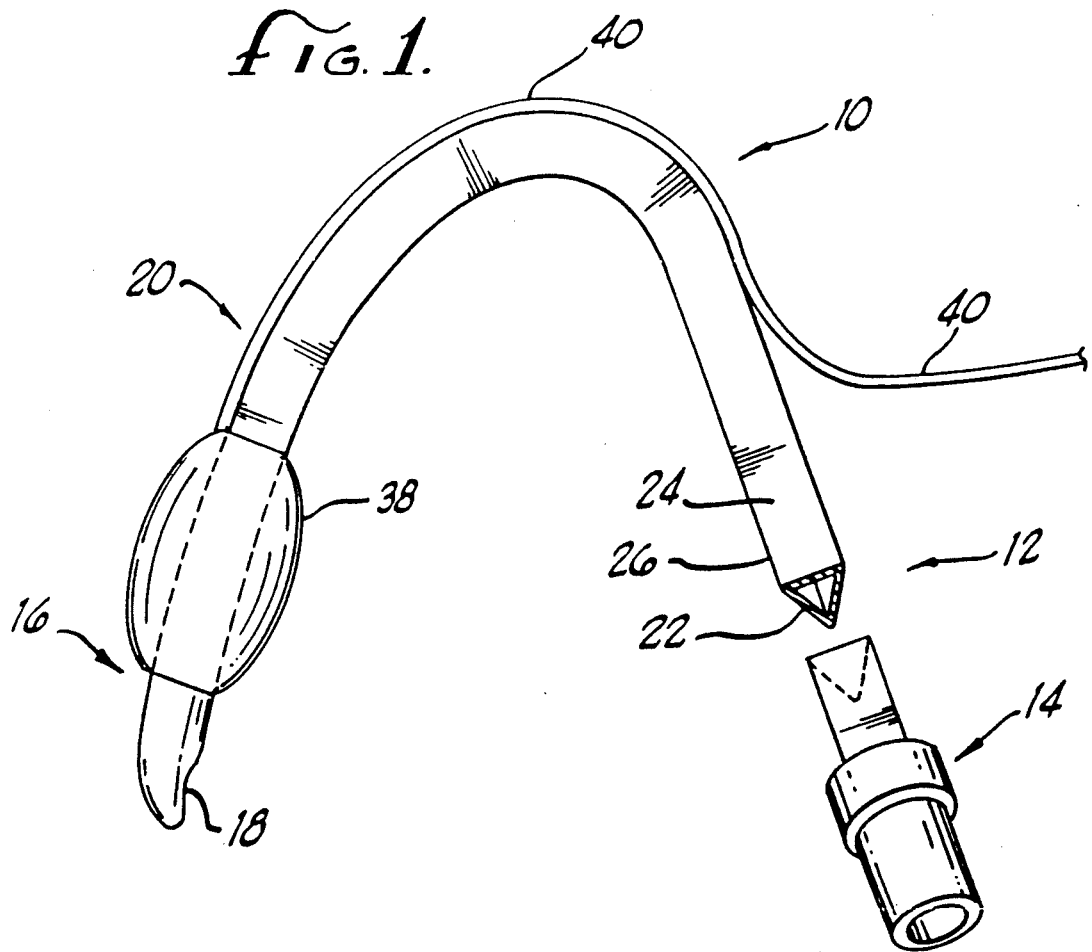
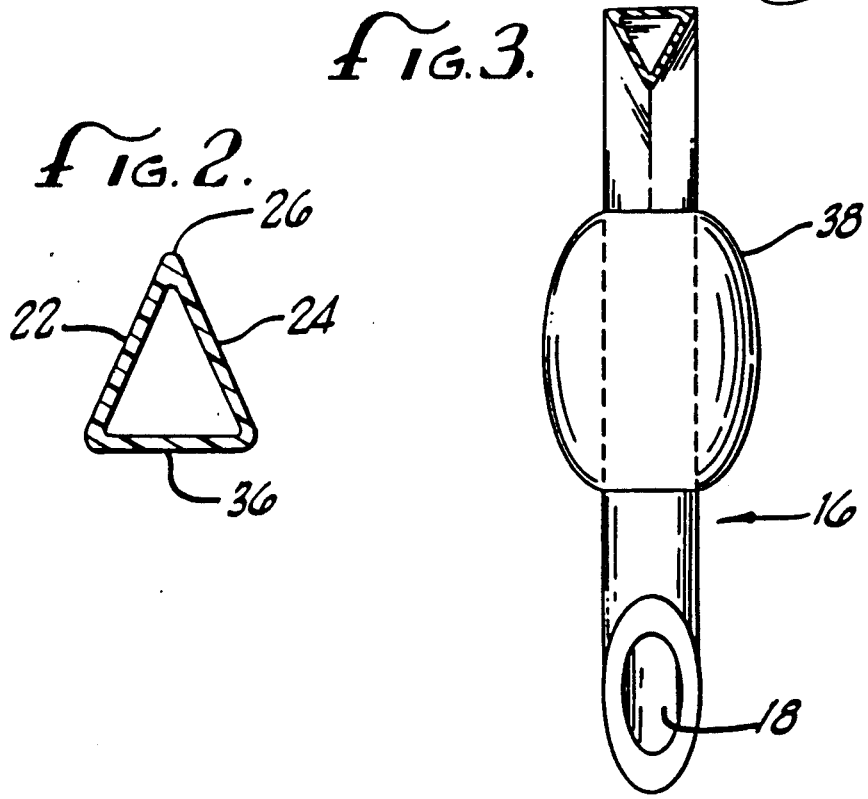

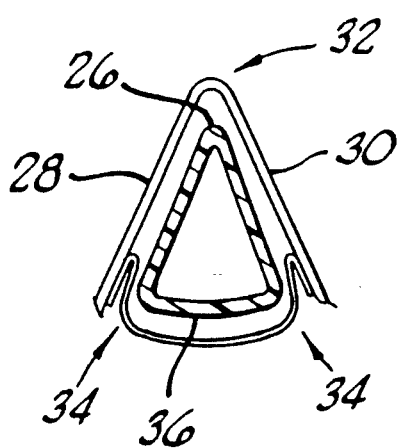
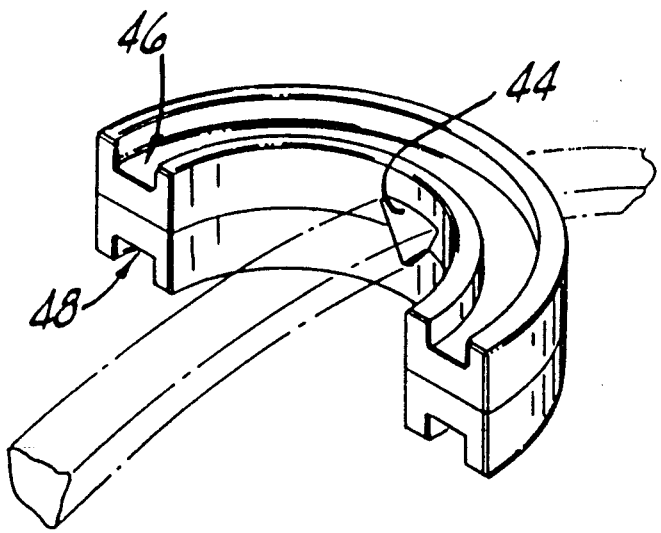
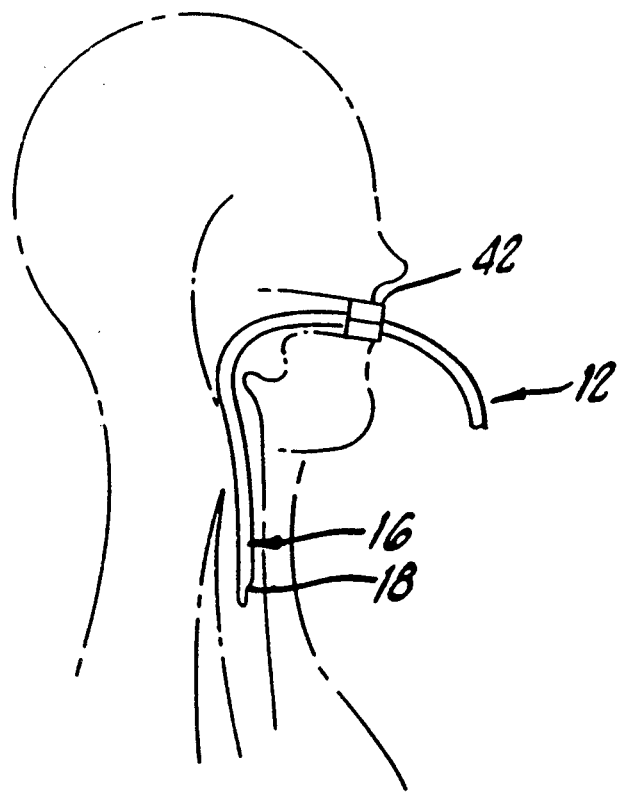

ENDOTRACHAEL TUBE

BACKGROUND OF THE INVENTION

1. Field of the Invention

This invention relates to endotracheal tubes, and more specifically to endotracheal tubes having a portion with an angular cross section.

2. Related Art

Endotracheal tubes have been used extensively in medical applications for ventilating a patient, for example during surgery, after lung failure, and for suction. Endotracheal tubes are round in cross section, both internally and externally, and are generally suitable for short surgeries. However, during long surgery or prolonged ventilation, contact between the round external surface of the endotracheal tube causes irritations in the vocal cords in the area where the tube makes contact. The irritation produces erosion of the vocal cord area where the prolonged contact occurs.

Irritation to the vocal cords is produced when the rounded surface of present endotracheal tubes makes prolonged contact with the vocal cords. Because the vocal cords have two parts which are angled with respect to each other, the inside surfaces of the vocal cords converge, when viewed in a transverse cross section, to a point. Each side of the vocal cords is relatively straight so that when the round tube contacts the vocal cords, for example due to bending or movement of the tube, it is believed that the entire force of any tube contact with the vocal cords is concentrated at the points on the vocal cords tangent to the rounded surface of the tube. This localizes the contact between the tube and the vocal cords, thereby ultimately producing irritation and inflamation.

There is a need, therefore, for an endotracheal tube which minimizes the possibility of contact between the tube and the vocal cords, and in the case of any such contact, distributes the force of the contact over a wide area. The endotracheal tube should still be flexible to allow the tube to be passed along the trachea and below the vocal cords. The present invention provides such an endotracheal tube.

SUMMARY OF THE INVENTION

The present invention is embodied in an endotracheal tube having an outer shape which minimizes the possibility of contact between the tube and the vocal cords, and in the event such contact is made, distributes the force of the contact over a large area between the tube and the vocal cords. The endotracheal tube according to the present invention includes a proximal end for attachment to an adapter or to another tube and a distal end having an opening for extending past the vocal cords of a patient. The tube includes an intermediate portion which passes between the vocal cords wherein the intermediate portion comprises an outer shape in transverse cross section defined in part by two substantially straight sides converging to a tip. With the substantially straight sides and the angled relationship between them, the tube can more easily pass between the vocal cords with less chance that there will be contact between the tube and the vocal cords. During prolonged ventilation, for example, there is still a possibility that there will be contact between the tube and the vocal cords, but the force of such contact is distributed over a larger surface area between the vocal cords and the surface of the tube.

In a preferred embodiment, the outer shape of the tube is further defined by a third side opposite the tip for forming a closed shape wherein the third side is curved outward away from the tip. Additionally, the inside shape of the tube is similar to the outside shape of the tube so that the cross sectional area of the passage way through the tube, for a given wall thickness, is greater than that for presently designed round tubes.

In a further embodiment, a mouthpiece is provided having an opening conforming to the outside shape of the tube. Use of the mouthpiece, for example during surgery, assist in preventing rotation of the tube while it is in place, in part because the outer shape of the tube is no longer round.

Consideration of the invention will now be made in more detail in conjunction with the following drawings.

BRIEF DESCRIPTION OF THE DRAWINGS

FIG. 1 is a side elevation view of an endotracheal tube in accordance with the present invention and an adapter therefore.

FIG. 2 is a transverse cross section of an intermediate portion of the endotracheal tube of FIG. 1.

FIG. 3 is an anterior elevation view and partial section of the endotracheal tube of FIG. 1.

FIG. 4 shows a portion of an endotracheal tube according to the present invention passing between vocal cords.

FIG. 5 is a lateral section and schematic of a patient showing the endotracheal tube in place with a mouth guard around the tube.

FIG. 6 is a perspective view of a mouthguard for use with the endotracheal tube of FIG. 1.

DETAILED DESCRIPTION OF THE PREFERRED EMBODIMENTS

An endotracheal tube will be described which has an outer shape for minimizing the possibility of contact with the vocal cords and adjacent tissue, and provides for a larger internal cross sectional area for air flow and for other functions. An endotracheal tube 10 (FIG. 1) has a proximal end 12 for attachment to an adapter 14 or to another tube (not shown). The endotracheal tube also includes a distal end 16 having an opening 18 for extending past the vocal cords of a patient. The tube includes an intermediate portion 20 which passes between the vocal cords wherein the intermediate portion comprises an outer shape which, in transverse cross section, is defined in part by two substantially straight sides 22 and 24, respectively, converging to a tip 26 (FIG. 2).

As depicted in FIG. 4, the human vocal cords have left and right sides, 28 and 30, respectively, which are angled with respect to each other when viewing the neck region in transverse section. The left and right sides converge to an anterior portion 32 where the space between the two sides is the narrowest. The left and right sides diverge away from the anterior portion to the arytenoid cartilage depicted at 34, forming an outwardly curved third side opposite the anterior portion 32. With the passageway defined by the left and right sides of the vocal cords and the arytenoid cartilage, an endotracheal tube, such as that shown in FIG. 2 having first and second sides converging to a tip is a more suitable configuration for a tube than the preexisting round tubes. Therefore, an endotracheal tube having two sides corresponding to the left and right vocal cords which are substantially straight are more suitable for long-term ventilation than round tubes. The substantially straight sides conform more closely to the shapes of the vocal cords. As a result, the likelihood that one or both sides of the tube will contact the vocal cords is decreased as compared to a round tube. Additionally, if contact between one of the sides and a corresponding side of the vocal cords occurs, the force of the contact is spread out or distributed over a larger surface area of the vocal cord, thereby minimizing the degree of damage to the vocal cords at any particular point of contact.

FIG. 2 shows one preferred configuration of the endotracheal tube wherein the first and second sides are of the same length and are joined at their divergent ends by a straight third side 36 opposite the tip. The angles between those two sides and the third side 36 are preferably between 30 and 45 degrees. The outside shape of the intermediate portion of the tube is therefore substantially triangular with smooth corners, to minimize any possible damage due to sharp corners.

The walls of the disclosed embodiment of the tube are of uniform thickness so that the inside walls of the tube are also substantially triangular. This provides a maximum interior cross sectional area for passage of air and instruments. For a given wall thickness, the cross sectional area of the passage way of a tube having a triangular cross section is greater than the cross sectional area of a correspondingly sized round tube.

Referring back to FIG. 1 in the disclosed embodiment, the triangular internal and external shape of the tube extends from the intermediate portion 20 to the proximal end 12. This maximizes the length of the tube which has the higher internal cross sectional area and provides for easier manufacture than if the proximal portion were round. In one form of the endotracheal tube, the internal cross sectional area of the distal end may be substantially less than the cross sectional area of the intermediate portion.

The endotracheal tube includes an inflatable low pressure cuff 38 well known to those skilled in the art. The cuff is inflated through an inflation tube 40 having an appropriate valve as would be known to one skilled in the art. The top of the cuff, as shown in FIG. 1, is located at the approximate transition point between the triangular shape of the intermediate portion 20 and the round configuration of the distal end 16. The transition is preferably gradual. FIG. 3 shows a gradual transition from the triangular outside shape of the tube to the circular shape. When in place in a patient, the cuff and the distal portion of the tube extend below the vocal cords.

At the proximal end of the tube, the first and second sides 22 and 24, respectively, and the tip 26 can be seen. The triangular proximal end joins with a complimentary triangular tipped adapter 14 so that the end of the endotracheal tube can be coupled to other equipment as is well known in the art. For example, the adapter may include a round end opposite the triangular end for coupling to a hose.

In an alternative embodiment of the endotracheal tube, the third side 36 is curved outwardly away from the tip 26 an amount which compliments the curvature of the arytenoid cartilages 34 and the space between them (the cricoid cartilage). (See FIG. 4.) The curvature will distribute the force resulting from contact between the third side and the arytenoid cartilage.

The endotracheal tube can be passed through the oral cavity of a patient so that the distal end passes through the area defined by the vocal cords and the arytenoid cartilage and below the vocal cords. The distal end is passed sufficiently below the vocal cords so that the cuff can be inflated below the vocal cords. While the endotracheal tube is in place, the straight, converging first and second sides of the intermediate portion of the endotracheal tube compliment the substantially straight sides of the vocal cords. Any contact between the first and second sides and the vocal cords is minimized in this configuration and any contact that may occur distributes the force of such contact over a larger area. This is significant where the endotracheal tube is to remain in place for an extended time.

Where the angular outside shape of the endotracheal tube extends a substantial distance toward the proximal end, a mouth guard 42 (FIGS. 5 and 6) can be used having an angular opening 44 through the middle thereof conforming to the outside shape of the endotracheal tube. Use of such a mouth guard minimizes the possibility of the endotracheal tube rotating while it is in place, in view of the angular configuration of the tube. The mouth guard includes an upper groove 46 for accepting the maxillary teeth and a lower groove 48 for accepting the mandibular teeth. One side, the right side as shown in FIG. 6, of the mouth guard is split from the right end to the opening 44 so that the upper and lower sections of the mouth guard can be separated and the tube positioned in the opening 44. The upper and lower sections can then be rejoined to allow the patient to bite the mouth guard.

The endotracheal tube and the fitting 14 are formed from materials from which current tubes and adapters are made. The tube may be formed from a suitable soft plastic and the adapter 14 may be formed from a suitable hard plastic.

An improved endotracheal tube and mouth guard therefor have been described. The endotracheal tube minimizes the possibility of there being contact between the sides of the tube and the vocal cords. However, if there is such contact, the force of the contact is distributed over a relatively larger surface area. This is accomplished by the endotracheal tube having an outside shape for that portion resting between the vocal cords, in transverse cross section, defined in part by two substantially straight sides converging to a tip. Where this angular configuration is extended sufficiently toward the proximal end of the tube, a mouth guard having a complimentary angular opening can be used to substantially prevent rotation of the tube while the tube is in place.

Although the present invention has been described in detail with reference only to the presently preferred embodiments, it will be appreciated by those of ordinary skill in the art that various modifications can be made without departing from the invention. Accordingly, the invention is limited only by the following claims.

I claim:

1. A flexible endotracheal tube having a proximal end for attachment to an adapter or to another tube, a distal end having an opening for extending past vocal cords of a patient and an intermediate portion for passing between the vocal cords and extending toward the proximal end and wherein the intermediate portion has a length when in place during normal use to extend outwardly of the patient's mouth and includes an outer shape in transverse cross section defined by two substantially straight sides converging to a tip and a third side opposite the tip for forming a closed shape, wherein the third side is curved outwardly away from the tip in an amount that compliments the curvature of the arytenoid cartilage, a mouthguard for placing in a patient's mouth to prevent biting by the patient of the tube and having a wall defining an opening conforming substantially to the outer shape of the intermediate portion.

2. The endotracheal tube of claim 1 wherein the intermediate portion further comprises an inside wall defining a channel in the tube wherein the shape of the wall of the channel is the same as the outer shape of the intermediate portion of the tube.

3. The endotracheal tube of claim 2 wherein the proximal end has an outer shape which is the same as the outer shape of the intermediate portion and has an inside wall defining a channel in the proximal end of the tube wherein the shape of the inside wall is the same as the shape of the inside wall of the intermediate portion.

4. The endotracheal tube of claim 1 wherein the distal end comprises a round outer shape and a round inner wall.

5. The endotracheal tube of claim 4 wherein the inside wall of the intermediate portion comprises a first cross sectional area and the inner wall of the distal end comprises a second cross sectional area less than the first cross sectional area.

6. The endotracheal tube of claim 1 wherein the outer shape of the intermediate portion is substantially triangular and wherein the opening in the mouthguard is substantially triangular.

7. The endotracheal tube of claim 1 wherein the two sides define an angle between the two sides of between approximately 30 degrees and 45 degrees.

8. The endotracheal tube of claim 1 wherein the tip is rounded.

9. A flexible endotracheal tube having a distal end having an approximately round outer surface and further comprising an intermediate tube portion having an outer shape in transverse cross section defined by first, second and third sides wherein the first and second sides are substantially straight and substantially equal in length and converge to a tip and wherein the third side connects the first and second sides opposite the tip and is curved to approximately the curvature of a posterior portion of a space between vocal cords of a patient, and comprising a mouthguard for placing in a patient's mouth to prevent biting by the patient of the tube and having a wall defining an opening conforming substantially to the outer shape of the intermediate tube portion.

10. The endotracheal tube of claim 9 wherein the primary tube section comprises a wall defining a channel and wherein the wall has a shape in transverse cross section substantially the same as the outer shape of the intermediate tube portion.

11. The endotracheal tube of claim 9 further comprising a mouthguard having a wall defining an opening through the mouthguard for surrounding the tube where the tube is to pass between a patient's teeth wherein the wall is shaped to conform to the sides of the tube.

12. The endotracheal tube of claim 11 wherein the mouthguard is curved from one end to another end in a horizontal plane to conform to the bite of a patient's teeth and wherein the mouthguard includes a horizontally extending split between one end of the mouthguard and the opening allowing placement of the mouthguard around the tube.

13. The endotracheal tube of claim 12 wherein the endotracheal tube has a longitudinal shape substantially in the form of a C.

* * * * *